United States Patent [19]

Sparkes et al.

[11] Patent Number: 4,572,906

[45] Date of Patent: Feb. 25, 1986

[54] CHITOSAN BASED WOUND DRESSING MATERIALS

[75] Inventors: Brian G. Sparkes, Toronto; Douglas G. Murray, Willowdale, both of Canada

[73] Assignee: Her Majesty the Queen in right of Canada, as represented by the Minister of National Defence of Her Majesty's Canadian Government, Ottawa, Canada

[21] Appl. No.: 656,851

[22] Filed: Oct. 2, 1984

[30] Foreign Application Priority Data

Nov. 21, 1983 [CA] Canada ............................ 441609

[51] Int. Cl.$^4$ .................. A61F 13/00; A61K 37/00; A61K 31/70; C09D 3/04
[52] U.S. Cl. ................................. 514/21; 106/125; 106/126; 106/128; 424/28; 514/55
[58] Field of Search ............... 424/28, 180; 106/125, 106/126, 128; 128/156; 514/21

[56] References Cited

U.S. PATENT DOCUMENTS

| | | | |
|---|---|---|---|
| 2,579,367 | 12/1951 | Curtis | 424/28 |
| 2,824,559 | 2/1958 | Sullivan et al. | 523/111 |
| 3,053,661 | 9/1962 | Starck et al. | 524/22 |
| 3,164,560 | 1/1965 | Suter | 524/22 |
| 3,558,771 | 1/1971 | Balassa | 424/28 |
| 3,597,374 | 8/1971 | Nagan | 524/23 |
| 3,632,754 | 1/1972 | Balassa | 424/180 |
| 3,767,784 | 10/1973 | Gluck | 424/180 |
| 3,903,268 | 9/1975 | Balassa | 424/28 |
| 3,911,116 | 10/1975 | Balassa | 424/28 |
| 3,914,413 | 10/1975 | Balassa | 424/28 |
| 4,243,656 | 1/1981 | Walliczek | 424/28 |
| 4,265,233 | 5/1981 | Sugitachi et al. | 128/156 |
| 4,383,022 | 5/1983 | Berger | 430/227 |
| 4,474,769 | 10/1984 | Smith | 424/180 |

*Primary Examiner*—Theodore Morris
*Attorney, Agent, or Firm*—Cushman, Darby & Cushman

[57] ABSTRACT

The invention disclosed is a surgical dressing, particularly useful for the protection of wounds during the healing process. The dressing comprises a blend of gelatin and chitosan in a weight ratio of about 3:1 to 1:3 and a compatible plasticizer in an amount of 0–40% w/w based on the combined weight of gelatin and chitosan.

16 Claims, No Drawings

CHITOSAN BASED WOUND DRESSING MATERIALS

This invention relates to surgical dressings for covering wounds, lesions or the like, in the form of a continuous wound-adherent film which protects the wound during the healing process, and in particular to a wound dressing material comprising gelatin and a polymer which includes (free) amine groups available for complexing (cross-linking) with gelatin.

One such polymer is chitosan. Chitosan is a cationic biopolymer formed by deacetylation of the polysaccharide chitin, which is the main structural component of the exoskeleton of insects, spiders and crustaceans.

Because the cost of isolating chitin from the giant piles of shrimp, lobster, and crab shells discarded by shellfish processors is not excessive, there has been great interest in developing commercial uses for this biopolymer; many important applications for chitin and chitosan have been found already in fields such as waste water clarification, animal nutrition, and medicine. The vigor of the hydrolysis conditions used by the manufacturer in the conversion of chitin to chitosan determines the molecular weight of the chitosan. One indication of molecular weight is the viscosity of a solution of the material. One North American manufacturer, Bioshell Incorporated of Albany, Oreg., measures the Brookfield viscosity of a 1% solution in 1% aqueous acetic acid at 25° C. and defines a high viscosity grade as 700-1000 cp, a medium viscosity grade as 250-650 cp, and a low viscosity grade as <250 cp.

The gelatin employed may be obtained from various sources such as bovine ossein, bovine skin, and pig skin, and be in a Bloom # range of 80-350.

A very large number of people are seriously burned in domestic and industrial accidents every year, and the number of these victims which dies in spite of intensive medical care is distressingly high. In Canada, the number of burn injuries requiring hospital admission approaches 25,000 per year. In the United States, about 130,000 are hospitalized annually because of burns; of these, 70,000 require intensive care at a cost exceeding $300,000,000, and 10,000 die.

The problem of burn treatment is even more acute in areas of the world in which there is armed conflict, since many of the weapons of modern warfare either directly or indirectly cause burns to both military personnel and civilians. In time of war the demands on medical facilities and supplies are very severe, and the mortality rate among burn victims is greatly increased.

In a third degree burn, the full thickness of the skin has been destroyed. The complete absence of "skin" cells in the burned area means that a new covering of skin will not spontaneously form there except by the very slow proliferation of healthy cells at the edges of the burn. One treatment is to remove a thin sheet of healthy skin from the patient's own body and graft it on the burned area. Only a partial thickness of skin is removed, so that the cells in the remaining layer of skin can regenerate a full thickness in the area from which the graft was harvested. In cases of burns covering 50% or more of the body surface area, this grafting procedure will be a lengthy process carried out in several stages because of the time required for regeneration of skin on the harvested sites.

In the intervening period between hospitalization and grafting, two very serious problems are caused by the absence of skin in the area of the burn. One of the most important functions of normal skin is to restrict the loss of body water by evaporation. The dramatic increase in water loss caused by destruction of the skin produces a large rate of heat loss due to the cooling effect of evaporation. In order to maintain a normal body temperature, the metabolic rate must increase, and a rapid depletion of fat and protein reserves ensues. The other serious problem caused by the absence of skin is bacterial invasion. If this invasive infection is not restricted, the high bacteria population makes the wound unsuitable for skin grafting. The victim of a major burn who receives no treatment for this infection will ultimately die from it.

After removal of the layer of dead tissue (eschar) lying on top of the burned area, it is desirable to cover the wound with a dressing which will control water loss and assist the body's own defences in controlling bacterial proliferation until skin grafting can be carried out.

Two natural materials, pig skin and human skin from cadavers, are regarded as very effective burn dressings. These materials can, under favourable circumstances, adhere to the wound very well and effectively control water loss and infection. One problem is that the body may recognize these biological materials as foreign substances, and begin a cellular response to reject them. Because of this, these biological dressings are usually replaced every 2 to 5 days. Another major drawback of these materials is their high cost. Cadaver skin at $80. and up per square foot, and pig skin at about $30. per square foot, are so expensive that physicians can be reluctant to use them except in cases in which they are essential for survival of the patient.

The disadvantages associated with these biological materials has given rise to the preparation of a large number of synthetic substitutes. The more effective of these have consisted of a foam, velour, or fibrous mat laminated to a synthetic resin film. Adhesion to the wound occurs by growth of tissue into the interstices of the foam or fibres, and the film controls loss of body water and prevents entry of bacteria. This basic approach has some inherent drawbacks. Since the adhesion depends on ingrowth, some time must elapse before the dressing is firmly adherent to the wound, and for this reason the pressing is usually secured to the wound with pressure dressings, sutures, or staples. A more serious problem in many cases has been the tenacious adherence that eventually does take place. Removal of the dressing can then be a traumatic procedure which may produce excessive bleeding and leave fragments of the synthetic material in the wound. These fragments may delay the healing of the wound when skin grafting is carried out.

A commercial laminate of this type with the trademark Biobrane is manufactured by Woodroof Laboratories, Inc. It is a composite of a flexible nylon fabric and an ultra-thin silicone rubber membrane. Although expensive (U.S. $40-50 per square foot), it is very effective on many types of open wounds such as granulation tissue, doner sites, and debrided second degree burns. Like most biological dressings such as pig skin, however, it performs relatively poorly on subcutaneous fat. This is unfortunate because early excision of third degree burn injuries usually exposes subcutaneous fat. Granulation tissue eventually does replace the fat, but there is a need in the intervening period for an effective, adherent wound covering.

A radically different type of burn dressing has been developed by I. V. Yannas and J. F. Burke and co-workers in the United States. Their approach has been to produce a material which slowly biodegrades at the wound surface and is assimilated by the body. During this biodegradation, the dressing not only restricts water loss and controls infections, but also acts as a tissue culture medium. Ultimately, migration of epidermal cells forms a new skin over the wound site. At the present state of development of their film, the healing of only relatively small wounds by this elegant process is possible. The film can be used to advantage on large wounds, but skin grafting is still required at a later stage. A commercial form of the film, when available, will probably be quite expensive.

Other useful wound dressings are described in applicant's co-pending Canadian applications Ser. No. 385,860 of Sept. 14, 1981, and Ser. No. 404,843 of June 10, 1982.

According to the present invention, a novel wound dressing material is contemplated, comprising a blend of gelatin and chitosan in a weight ratio of about 3:1 to 1:3, and a compatible plasticizer in an amount of 0–40% w/w based on the combined weight of gelatin and chitosan. In contrast to conventional wound dressing materials, this contemplated material displays excellent adhesion to subcutaneous fat.

According to another aspect of the invention, a novel method for making a wound dressing material is also contemplated, said material comprising gelatin and chitosan in a weight ratio of about 3:1 to 1:3, the method comprising (a) dissolving the chitosan in water in the presence of a suitable acid resulting in a pH in solution of about 2–5, (b) adding the gelatin dissolved in water, and (c) mixing.

In order to combine chitosan with a water soluble polymer such as gelatin, the chitosan should be dissolved in water. Chitosan will sufficiently dissolve in water if acid is added. Both organic and inorganic acids have been found to be satisfactory for preparing chitosan solutions suitable for use in the present invention. Examples of acceptable organic acids are acetic acid, formic acid and lactic acid. Acetic acid is not a preferred acid because it imparts an odour to the resulting films. An example of a acceptable inorganic acid is hydrochloric acid (HCl). Chitosan has been found to be insufficiently soluble in certain organic and inorganic polybasic acids, such as citric acid and phosphoric acid, for them to be useful.

It is important that a minimal amount of acid be used in the preparation of the chitosan solution so that (i) there will be as little acid as possible to neutralize in the final solution of chitosan and gelatin, and (ii) there will be minimal degradation of the chitosan during the dissolving process.

This is done by adding the acid in small portions over a period of one or more hours to a stirred suspension of the chitosan in water at about room temperature. The resulting solution, if prepared from commercial chitosan, may contain numerous gel particles (partially hydrolyzed chitin) and insoluble material (mainly chitin) which can be removed by filtration. The dry weight of the insoluble material can be of the order of 10% of the original dry weight of the chitosan.

After mixing the acidic chitosan solution with gelatin dissolved in distilled water, the pH is often less than 5. (i.e. about 2–5) Although a continuous wound-adherent film prepared by casting this solution of a flat plate and allowing it to dry is a useful burn dressing, it is desirable to raise the pH in order to minimize the possibility that the film will cause pain or tissue damage when applied to the wound. Direct addition of 5% aqueous sodium hydroxide or 5% aqueous ammonia causes precipitation of a gel. Much more dilute solutions of these bases might not cause precipitation, but they would cause too great a dilution of the gelatin/chitosan solution. It has been found that a satisfactory basic solution for raising the pH is 5% aqueous sodium bicarbonate. Another method which has been used to raise the pH is the basification of the gelatin solution before addition to the chitosan solution. Achieving pH values much greater than about 6.3 is not possible because of precipitation of the chitosan or a chitosan/gelatin complex. If the original chitosan solution is dissolved in hydrochloric acid, gelatin/chitosan (1:1 by weight) films prepared by casting solutions adjusted to pH 6.3 are often cloudy or develop white areas if subjected to light pressure such as when held between thumb and forefinger. This problem is greatly diminished when lactic acid is used in place of hydrochloric acid for dissolving the chitosan, and when a lower pH, such as 5.7, is used.

The data in Table I show that pH has little effect on flexibility in the range 4.3–6.3. The flexibility test used for these measurements was described in detail on page 14 of our Canadian Patent Application Ser. No. 385,860 filed Sept. 14, 1981. Unplasticized gelatin/chitosan films are relatively stiff. The data in Table II shows the improvement given by the addition of compatible plasticizers such as glycerol and sorbitol. Both are effective plasticizers. The sorbitol modified films are clearly less flexible.

TABLE I

Effect of pH on the flexibility of gelatin/chitosan films.

| Batch #[1] | Gelatin[2]: Chitosan[3] (parts by weight) | pH of gelatin/chitosan solution when cast[4] | Thickness of film sample (mm)[5] | Weight required to force 15 mm wide sample through a 6.5 mm gap.[6] |
|---|---|---|---|---|
| 229 | 1:1 | 4.3 | 0.061–0.064 | 21.6 g |
| 229 | 1:1 | 4.8 | 0.068–0.069 | 26.0 g |
| 229 | 1:1 | 6.3 | 0.065–0.069 | • 26.0 g |
| 230A | 1:1 | 5.7 | 0.065–0.068 | 23.2 g |
| 230A | 1:1 | 6.3 | 0.062–0.066 | 20.6 g |
| 230B | 1:2 | 5.7 | 0.049–0.050 | 8.8 g |
| 230B | 1:2 | 6.3 | 0.050–0.052 | 10.2 g |

Notes:
[1]Films with the same batch number were prepared using the same gelatin/chitosan solution.
[2]Ossein gelatin of Bloom #250.
[3]Chitosan of viscosity grade 970 cp.
[4]Hydrochloric acid was used to prepare the original chitosan solution; pH adjustment of the final gelatin/chitosan solution was done with 5% aqueous sodium bicarbonate.
[5]Range for several measurements in the central area of the film.
[6]Film strips were equilibrated at 35 ± 1% relative humidity at 20 ± 1° C. for 24 hours before the measurements which were made under the same conditions. The test is described in detail on page 14 of commonly assigned copending application Serial No. 406,523 filed August 9, 1982.

TABLE II

Flexibility and swelling properties of gelatin/chitosan films plasticized with glycerol and sorbitol. Gelatin/chitosan solutions were adjusted to pH 6.3 with 5% aqueous NaHCO$_3$ before they were cast and dried.

| Batch #[1] | Parts by weight gelatin (Bloom #), chitosan (viscosity), and plasticizer; acid used to dissolve chitosan | Weight required to force 15 mm wide sample through a 6.5 mm gap[2]; dry thickness[3] | % Increase in length when swollen in distilled water[4]; dry thickness[5] |
|---|---|---|---|
| 235 | 15 gelatin (250), 7 chitosan (630 cp), 0 plasticizer; HCl | 27.4 g; 0.078–0.084 mm | 67%; 0.080–0.083 mm |
| 235 | 15 gelatin (250), 7 chitosan (630 cp), 2.2 glycerol; HCl | 11.4 g; 0.080–0.085 mm | 77%; 0.080–0.083 mm |
| 235 | 15 gelatin (250), 7 chitosan (630 cp), 4.4 glycerol; HCl | 2.7 g; 0.085–0.089 mm | 77%; 0.085–0.087 mm |
| 235 | 15 gelatin (250), 7 chitosan (630 cp), 6.6 glycerol; HCl | 0.8 g; 0.094–0.099 mm | 90%; 0.085–0.090 mm |
| 235 | 15 gelatin (250), 7 chitosan (630 cp), 6.6 sorbitol; HCl | 4.1 g; 0.086–0.089 mm | 97%; 0.085–0.088 mm |
| 234 | 10 gelatin (250), 9 chitosan (130 cp), 0 plasticizer; HCl | 37.8 g; 0.094–0.097 mm | 124% 0.091–0.093 mm |
| 234 | 10 gelatin (250), 9 chitosan (130 cp), 2 glycerol; HCl | 19.4 g; 0.092–0.096 mm | 138%; 0.097–0.099 mm |
| 234 | 10 gelatin (250), 9 chitosan (130 cp), 2 sorbitol; HCl | 24.8 g; 0.089–0.090 mm | 121%; 0.093–0.096 mm |
| 233 | 10 gelatin (250), 9 chitosan (630 cp), 0 plasticizer; HCl | 81.8 g; 0.116–0.120 mm | 67%; 0.112–0.115 mm |
| 233 | 10 gelatin (250), 9 chitosan (630 cp), 2 glycerol; HCl | 48.6 g; 0.121–0.122 mm | 66%; 0.122–0.125 mm |
| 233 | 10 gelatin (250), 9 chitosan (630 cp), 2 sorbitol; HCl | 55.4 g; 0.120–0.123 mm | 76%; 0.119–0.122 mm |
| 236 | 10 gelatin (250), 9 chitosan (630 cp), 0 plasticizer; lactic acid | 109.0 g; 0.138–0.149 mm | 90%; 0.140–0.143 mm |
| 236 | 10 gelatin (250), 9 chitosan (630 cp), 2 glycerol; lactic acid | 23.2 g; 0.124–0.132 mm | 100%; 0.130–0.133 mm |
| 236 | 10 gelatin (250), 9 chitosan (630 cp), 4 glycerol; lactic acid | 3.4 g; 0.148–0.153 mm | 90%; 0.133–0.138 mm |

Notes:
[1] Films with the same batch number were prepared using the same gelatin/chitosan solution.
[2] Film strips were equilibrated at 51 ± 2% relative humidity and 24° C. for 13 hours (first 11 entries in table), or at 55 ± 2% relative humidity and 25–27° C. for 12.5 hours (last 3 entries), before the measurements, which were made under the same conditions. The test is described in detail on page 14 of (our) Canadian Application Serial No. 385,860 filed 14 September.
[3] Range for several measurements in the central area of the film.
[4] Film strips 15 × 30 mm of the stated dry thickness were gently agitated in 50 ml of distilled water at room temperature for 1 hour.
[5] Range for several measurements over the entire film area.

Although gelatin/chitosan films transmit water vapour very well, they will still swell a great deal when placed on wounds which are very moist because of rapid exudate production. However, they do have the very desirable property of swelling much more in thickness than in length and width. Because swelling in length and width places a shear stress on the adhesion of the film to the wound, it is important that swelling in these dimensions be as small as possible. A relative indication of the degree of swelling that a film may undergo when exposed to copious quantities of wound exudate is given by its swelling when immersed in distilled water. The last column of Table II shows that the presence of substantial amounts of glycerol and sorbitol do not have a large affect on the increase in length as a result of immersion in distilled water. It is thus contemplated that 0–40% w/w, preferably about 21% w/w of the plasticizer, based on the combined weights of gelatin and chitosan, can be usefully added.

Several of the films in Table II were prepared with chitosan of viscosity grade 130 cp. These films produced weak hydrogels when swollen in water, in contrast to the hydrogels from the viscosity grade 630 cp chitosan which were relatively strong. For this reason, viscosity grades in the range 150–1100 cp are contemplated. However a viscosity grade of about 500 cp is preferred.

It has been found that, on fresh excisions down to subcutaneous fat on the back of a juvenile domestic pig, some gelatin/chitosan films actually contract slightly, shortly after application. The results of tests on six different gelatin/chitosan preformed films are given in Table III. It was found that the presence of glycerol increased shrinkage. Use of lactic acid to dissolve chitosan caused more shrinkage than use of hydrochloric acid. Hydrochloric acid is thus preferred.

TABLE III

Shrinkage of gelatin/chitosan films on freshly excised wounds down to subcutaneous fat on the back of a juvenile domestic pig.

| Film[1] Parts by weight of each component; acid used to dissolve chitosan; thickness | Film Sample # | Length, to nearest 0.5 mm, of film strips 40 mm long after 0.5 hr. and 4.0 hr. on the wound | |
|---|---|---|---|
| | | 0.5 hr. | 4.0 hr. |
| 10 gelatin, 9 chitosan; HCl; 0.11 mm | 1 2 | 40.5 40 | 40.5 40 |
| 10 gelatin, 9 chitosan; lactic acid; 0.11 mm | 1 2 | 39 39 | 39 39 |
| 15 gelatin, 7 chitosan; HCl; 0.08 mm | 1 2 | 39 38.5 | 39 38.5 |
| 15 gelatin, 7 chitosan, 6.6 glycerol; HCl; 0.09 mm | 1 2 | 37[2] 38[3] | 37 38 |
| 10 gelatin, 9 chitosan, 4 glycerol; lactic acid., 0.14 mm | 1 2 | 38[2] 38.5[2] | 38 38 |
| 10 gelatin, 9 chitosan, 6 glycerol; HCl; 0.13 mm | 1 2 | 38.5[2] 39 | 38 38.5 |

Notes:
[1]Cattle ossein gelatin, Bloom #250, was used. The chitosan was viscosity grade 630 cp. All films were prepared from solutions adjusted to pH 6.3 before casting.
[2]Top surface of film was slightly tacky.
[3]Top surface of film was tacky.

The effects of film composition on adhesion to subcutaneous fat was determined by placing films on freshly excised wounds down to about the middle of the top fat layer on the backs of juvenile domestic pigs. The films are not secured to the wounds by any means other than natural adhesion, and no other dressing was placed on top. The degree of adhesion was assessed subjectively immediately after placement on the wound, at three or four days, and at seven days. The results are given in Table IV. The performance of all film compositions was generally satisfactory. The relatively poor result in entry #4 was anomalous since the same film in entry #3 did extremely well on another site. Over the seven day period there was a gradual loss of adhesion at the edges of the wounds. A thick, crusty exudate developed in the gap between the edge of the film and the edge of the wound, and the growth of the exudate and granulation tissue in this gap contributed to the dislodgement of the film at the periphery. In addition, forces caused by the animals' movements which tend to disrupt the adhesion will be greater at the edges than at the centre. Hospitalized burn patients would be much less active and may in fact have the affected areas immobilized; under clinical conditions, therefore, disruption of adhesion will be much less likely.

Removal of adherent wound dressings can be very traumatic in terms of pain for the patient and damage to the wound bed. Although the gelatin/chitosan films normally exhibit a strong adhesion to the wound, this adhesion is lost when the films are converted to the hydrogel by swelling in water or physiological saline solution. For example, after seven days of continuous adhesion to the wounds, the films in entries #2, #3, #8, and #9 in Table IV were soaked in physiological saline for ten minutes. At the end of this time all of the films had little or no adhesion to the wound, and could be easily pulled off as intact sheets.

TABLE IV

Adhesion of various formulations of gelatin/chitosan films to freshly excised wounds down to the middle of the top layer of fat on the backs of juvenile domestic pigs.

| Entry # | Film[1] Parts by weight of each component; acid used to dissolve chitosan; thickness | Subjective assessment of adhesion of film to wound; area of wound to which adhesion had been maintained. |
|---|---|---|
| 1 | 5 gelatin, 7 chitosan (630 cp); HCl; 0.08 mm | 0 days: excellent 3 days: excellent; 90% 7 days: excellent; 75% |
| 2 | 1 gelatin, 1 chitosan (970 cp); HCl; 0.06 mm | 0 days: fair-good 4 days: very good; 65% 7 days: very good; 30% |
| 3 | 10 gelatin, 9 chitosan (630 cp); HCl; 0.12 mm | 0 days: good 4 days: very good; 90% 7 days: very good; 80% |
| 4 | 10 gelatin, 9 chitosan (630 cp); HCl; 0.12 mm | 0 days: very good in centre, poor at corners 3 days: fair; 5%; film removed |
| 5 | 10 gelatin, 9 chitosan (630 cp); lactic acid; 0.14 mm | 0 days: excellent in centre; poor at corners 3 days: excellent; 50%; film removed |
| 6 | 10 gelatin, 9 chitosan (630 cp), 4 glycerol; HCl; 0.12 mm | 0 days: excellent 4 days: very good; 80% 7 days: excellent; 50% |
| 7 | 10 gelatin, 9 chitosan (630 cp), 4 glycerol; lactic acid; 0.14 mm | 0 days: excellent 3 days: excellent; 90% 7 days: excellent; 75% |
| 8 | 10 gelatin 9 chitosan (630 cp), 6 glycerol; HCl; 0.13 mm | 0 days: excellent 4 days: very good; 75% 7 days: very good; 50% |
| 9 | 15 gelatin, 7 chitosan (630 cp), 6.6 glycerol; HCl; 0.09 mm | 0 days: good 4 days: very good; 75% 7 days: good; 60% |

Notes:
[1]Cattle ossein gelatin, Bloom #250, was used. All films were prepared from solutions adjusted to pH 6.3 before casting.

Although wound contraction is a normal part of the healing process, in the severely burned patient it can lead to rigid scars which, in addition to causing disfigurement, can produce a crippling loss of normal motion. Gelatin/chitosan films have the ability to retard contraction. This is shown in Table V, in which the product of the wound length and width at eight days is compared with that when the dressings were initially applied. The ratio for the site which had the control film of vaseline gauze was 23-45% lower than that of the three sites which had the gelatin/chitosan film.

TABLE V

Inhibition of contraction of a freshly excised wound down to subcutaneous fat[1] by a gelatin/chitosan film over a period of 8 days.

| Wound Dressing | Observation at 8 days | $\frac{\text{Length}^4 \times \text{width}^4 \text{ at 8 days}}{(\text{original length} \times \text{width})} \times 100\%$ |
|---|---|---|
| vaseline gauze[2] | Healthy granulation tissue had formed | $\frac{30 \times 36 \text{ mm}}{39 \times 40 \text{ mm}} \times 100 = 69.2\%$ |

TABLE V-continued

Inhibition of contraction of a freshly excised wound down to subcutaneous fat[1] by a gelatin/chitosan film over a period of 8 days.

| Wound Dressing | Observation at 8 days | $\frac{\text{Length}^4 \times \text{width}^4 \text{ at 8 days}}{\text{(original length} \times \text{width)}} \times 100\%$ |
|---|---|---|
| gelatin/chitosan[3] | Film remained adherent to 80% of original area; adhesion excellent. | $\frac{35 \times 37 \text{ mm}}{38 \times 37 \text{ mm}} \times 100 = 92.1\%$ |
| gelatin/chitosan[3] | Film remained adherent to 70% of original area; adhesion excellent. | $\frac{35 \times 37 \text{ mm}}{40 \times 38 \text{ mm}} \times 100 = 85.2\%$ |
| gelatin/chitosan[3] | Film remained adherent to 50% of original area; adhesion very good. | $\frac{36 \times 36 \text{ mm}}{35 \times 37 \text{ mm}} \times 100 = 100.1\%$ |

Notes:
[1]Middle of the top fat layer on the back of a juvenile domestic pig.
[2]Control dressing of Bactigras ® (Smith and Nephew, Incorporated, Lachine, Quebec). It was replaced with fresh Bactigras at 4 days.
[3]Film was a 1:1 mixture of cattle hide gelatin of Bloom #150 and chitosan of viscosity grade 970 cp. The gelatin/chitosan solution was adjusted to pH 4.8 just before it was cast. Thickness was 0.08 mm.
[4]Length is defined as parallel to the spine and width as perpendicular to the spine. Measurements were made in the centre of the wound from hairline to hairline.

Instead of allowing a layer of gelatin/chitosan solution to dry to a film of a flat plate and then applying that preformed film to a wound, there are advantages to direct coating of the gelatin/chitosan solution on a wound and letting it dry to a film in situ. Because a liquid can flow into depressions and crevices, there are no air spaces left to become filled with exudate and possibly be converted to sites of localized infection. In addition, the larger area of contact as compared with application of a preformed film can produce a superior overall adhesion. Unfortunately, the gelatin/chitosan solutions used to prepare the films dry too slowly, and they do not form gels on the wound soon after application but remain as viscous liquids until close to dryness. A method has been discovered for producing a tough outer gel layer on the top of the freshly applied gelatin/chitosan liquid coating. This consists of adding a solution of a setting agent, which may be the salt of a polyvalent cation which can crosslink the polymers by forming bonds to anionic sites, or a basic solution which can raise the pH of the liquid, thereby causing formation of a gel of chitosan or of a complex of chitosan and gelatin. Many basic agents can be used. However, those which would give solutions which are highly caustic should be avoided because of the hazard of accidental contact with healthy tissue. Examples include NaOH, NH$_3$ and Na$_2$CO$_3$. Two setting agents which have proven very effective are zinc acetate and sodium bicarbonate. The preferred method of application of these setting agents is to soak an absorbent, flat pad of paper or cloth with an aqueous solution and lay it on the freshly applied gelatin/chitosan liquid for about one minute; the pad can then be easily removed. The newly formed outer layer of gel on the surface of the gelatin/chitosan film is strong and only slightly tacky if at all. Beneath this gel there is a relatively mobile layer of gelatin/chitosan liquid. The outer gel layer and inner liquid layer eventually dry to a single, strong, transparent film. Preferred concentrations of zinc acetate and sodium bicarbonate are 2.5%/w and 9%/w respectively. When sodium bicarbonate or other suitable base is used, the pH of the gelatin/chitosan liquid applied to the wound should be close to the upper limit at which the polymers remain in solution, i.e. 6.0 to 6.3, preferably about 6.3. When no setting agent or when zinc acetate is used a pH range of 4.0-6.3 is envisaged.

Although use of a pad soaked in a solution of a setting agent is preferred, other methods can be envisaged, such as spraying a fine mist of the solution on the liquid or applying the setting agent as a dry powder by shaking or spraying. A successful procedure used in initial experiments consisted of placing drops of the setting agent solutions directly on the liquid and then gently "patting" them by hand to spread them out.

Tests of a liquid composed of 10 parts gelatin (ossein; Bloom #250), 9 parts chitosan (viscosity grade 630 cp; dissolved with hydrochloric acid), 4 parts glycerol, and 470 parts water, and adjusted to pH 6.3, were carried out on fresh excised wounds down to the top layer of subcutaneous fat on the backs of juvenile domestic pigs. On two sites the liquid was applied alone; no setting agent was used. Drying of the film was almost complete after one hour. When examined after seven days, the film had a few long cracks with gaps between the broken edges. These cracks may have been due to contraction of the film during drying. The adhesion to the wound, assessed subjectively, ranged from very good to excellent. The film was left on one of the sites for an additional three days, after which it still had very good adhesion. On a third site, the same liquid was set with an aqueous solution of zinc acetate. After seven days, the film was not cracked, and had excellent adhesion to 75% of the original wound area.

EXAMPLE 1

Sixteen grams of chitosan (from Bioshell, Incorporated; Lot 2200; viscosity grade 630 cp) were suspended in 750 ml of distilled water and stirred at about 60 rpm at room temperature with a motor driven rod fitted with three impellers 72 mm in diameter. About one ml of concentrated hydrochloric acid was added dropwise to the stirred mixture over a period of one minute. After ten minutes, another one ml was added dropwise. This was repeated at 10 to 15 minute intervals until a total of 7 additions (7 ml or about 3.1 grams of hydrochloric acid) had been made. The initial pH of the suspension was 5.8. Ten to fifteen minutes after the addition of each of the first six 1 ml portions of concentrated hydrochloric acid, the pH was 4.5 to 5.0. Twenty minutes after the final addition, it was 2.3. After another 60 minutes, it had risen to 3.0. At this point there were still swollen, transparent gel particles and white flakes left in the viscous solution.

Sixteen grams of cattle ossein gelatin (Knox Brand; Thomas J. Lipton Company; Bloom #250) were dissolved in 90 ml of distilled water at about 50° C. The warm gelatin solution was added to the chitosan solution prepared above and the mixture was stirred for 30 minutes. At the end of this time the pH was 4.8. A 5% aqueous solution of sodium bicarbonate was added dropwise with stirring in portions of about 5 ml over a period of approximately 2 hours until the pH had risen to 5.7. A total of about 43 ml or 2.2 grams of sodum bicarbonate was required. A solution of 6.4 grams of glycerol in 20 ml of distilled water was added, and the mixture was stirred for 15 minutes. The solution was filtered through a 70 mesh polyester screen using mild suction to remove insoluble material present in the original chitosan solution. When dry, the residue from the filtration weighed 3.1 grams. The viscous liquid left a thick film on the inside of the containers when it was poured out. The losses of viscous solution as a thick residual film on the filtration apparatus and filter left only 550 ml of filtrate. This filtrate was too viscous for the bubbles to rise to the surface in a reasonable length of time. A satisfactory viscosity was achieved by dilution with 100 ml of distilled water. The solution was cast on a sheet of polystyrene to dry in the normal room atmosphere. The dry film removed from the sheet after 7 days had a thickness of about 0.1 mm and was transparent except for a faint, cloudy ring near the periphery.

EXAMPLE 2

(Illustrating a single addition of hydrochloric acid, which is not preferred, and the elevation of pH by the addition of a basified gelatin solution, which is also not preferred.)

Four grams of chitosan flakes (from Bioshell, Incorporated; Lot 2065; 970 cp) were stirred at room temperature with a solution of 1.75 g of concentrated hydrochloric acid in 200 ml of distilled water for 11 hours and then left overnight. Some insoluble material was removed from the viscous solution by means of a pipette having a large opening. The solution, whose pH was 1.8, was warmed to about 30° C. prior to mixing with the gelatin solution described below. A solution of 4 g of gelatin (retail grade, Davis Gelatine Company; hide gelatin; Bloom #150) in 80 ml of distilled water was prepared and, while at about 30° C., its pH was raised to 9.8 by the addition of aqueous sodium hydroxide. Within minutes of adjustment to pH 9.8, the warm gelatin solution was added in portions with vigorous stirring to the warm chitosan solution. Stirring was continued for 7 minutes after completion of the addition. At the end of this time the homogenous mixture had a pH of 4.8. The film obtained after casting this solution and drying at ambient temperature and humidity had a thickness of 0.09 mm and was slightly hazy.

EXAMPLE 3

A suspension of 15.5 grams of chitosan (from Bioshell, Incorporated; Lot 2200; viscosity grade 630 cp) in 750 ml of distilled water was stirred as in Example 1 at room temperature while 1.0 ml of 88% aqueous lactic acid solution (Fisher Scientific; Product #A-162; mixture of D-lactic acid and L-lactic acid) was added dropwise. At intervals of 5 to 10 minutes, another 4 portions of 1 ml were added dropwise, followed by 2 portions of 0.5 ml each. Twenty minutes after the final addition of 0.5 ml, the pH was 4.5. In order to remove undissolved material, the very viscous solution was filtered through a J-Cloth ® towel (Johnson and Johnson; medium; #1633), which had previously been washed with distilled water. When dry, the insoluble material weighed 1.92 grams. The filtrate was warmed in preparation for addition of the gelatin solution described below.

Fifteen grams of gelatin (Knox Brand; Thomas J. Lipton Company; cattle ossein; Bloom #250) were dissolved in 60 ml of distilled water by warming. The warm solution was added to the warm chitosan solution. After thorough mixing, the pH was 4.8. Stirring was continued as a total of 35 ml of 5% aqueous sodium bicarbonate was added dropwise in portions of 2–5 ml; a period of 10 minutes was allowed between each portion. Ten minutes after completion of the final addition, the pH was 6.3.

Six grams of glycerol in 30 ml of distilled water were added. The mixture was stirred and then allowed to stand in a warm bath (30°–45° C.), for 5.5 hours in order for the majority of small bubbles to rise to the surface. The foam on top was then skimmed off and the solution, whose temperature was 36° C., was cast onto a polystyrene sheet and left to dry at ambient temperature and relative humidity. After 4 days, the dry film was removed from the plate; its thickness was 0.14 mm.

EXAMPLE 4 (Liquid)

A suspension of 18 grams of chitosan (from Bioshell, Incorporated; Lot 2200; 630 cp) in 750 ml of distilled water were stirred as in Example 1 and 1.0 ml of concentrated hydrochloric acid was added dropwise. Another 5 one ml portions of concentrated hydrochloric acid were added at intervals of 5–15 minutes. Thirty minutes after the addition of the final portion, the pH was 4.2. The mixture was allowed to stand for 45 minutes, and then was stirred for 15 minutes. At the end of this time the pH was 4.8. The very viscous solution was filtered by gravity through a piece of 70 mesh polyester sieve cloth. After the insoluble material had dried, it weighed 2.1 grams. The filtrate was warmed for the addition of the gelatin solution described below.

Eighteen grams of gelatin (Knox Brand; Thomas J. Lipton Company; ossein gelatin; Bloom #250) were dissolved in 60 ml of warm distilled water. The warm gelatin solution was mixed with the warm chitosan solution, and the pH of the mixture was raised from 4.8 to 6.3 by the addition of a total of 48 ml of 5% aqueous sodium bicarbonate dropwise in portions of 3–10 ml added at intervals of 5–10 minutes.

A solution of 7.2 grams of glycerol in 15 ml of distilled water was added and the mixture was stirred for about 15 minutes. It was allowed to stand in a warm bath to allow the bubbles to rise to the surface where they were skimmed off.

The solution is stored at about 4° C. At this temperature it sets to a gel which must be melted by gentle warming before use.

The embodiments of the invention in which an exclusive property or privilege is claimed are defined as follows:

1. A method for making a wound dressing material, said material comprising a blend of gelatin and chitosan in a weight ratio of about 3:1 to 1:3, the method comprising:
 (a) dissolving the chitosan in distilled water by adding lactic acid or hydrochloric acid in small portions over an extended time period to a stirred suspension of chitosan in water at about room temperature, the acid resulting in a pH in solution of about 2–5,
 (b) adding the gelatin dissolved in dissolved water,
 (c) mixing, and (d) adding a basic solution to raise the pH of the mixture so formed to about 5.7 to 6.3.

2. A method according to claim 1, wherein the basic solution is 5% aqueous sodium bicarbonate.

3. A method according to claim 2, including the additional step of (e) adding a compatible plasticizer selected from the group consisting of glycerol and sorbitol.

4. A method according to claim 3, including the additional step of
(f) casting the solution on a flat plate and drying to a continuous wound-adherent film.

5. A method according to claim 3, including the additional step of
(f) coating the solution onto a wound and drying in situ.

6. A method according to claim 5, which includes the additional step of
(g) apply a solution of a non-caustic setting agent onto the freshly applied coating to provide a tough outer gel layer.

7. A method according to claim 6, wherein the setting agent is selected from zinc acetate and sodium bicarbonate.

8. A method of treating a wound which comprises applying to the wound a wound dressing material in the form of a continuous preformed film, the material comprising a blend of gelatin and chitosan in a weight ratio of about 3:1 to 1:3 and a compatible plasticizer in an amount of 0-40% w/w based on the combined weight of gelatin and chitosan.

9. The method according to claim 8, wherein the weight ratio of gelatin to chitosan is about 1:1.

10. The method according to claim 9, wherein the plasticizer is selected from the group consisting of glycerol and sorbitol.

11. The method according to claim 8, wherein the chitosan is of a viscosity grade of about 630 cp and the gelatin has a bloom number of about 80 to about 350.

12. A method of treating a wound which comprises
(1) applying to the wound a coating of an aqueous solution of a burn dressing material comprising a blend of gelatin and chitosan in a weight ratio of about 3:1 to 1:3 and a compatible plasticizer in an amount of 0-40% w/w based on the combined weight of gelatin and chitosan, and allowing the thus applied coating to dry in situ; and
(2) applying a solution of a non-toxic setting agent on to the freshly applied coating to provide a tough outer gel layer.

13. The method according to claim 12, wherein the setting agent is selected from zinc acetate and sodium bicarbonate.

14. The method according to claim 12, wherein the weight ratio of gelatin to chitosan is about 1:1.

15. The method according to claim 12, wherein the plasticizer is selected from the group consisting of gylcerol and sorbitol.

16. The method according to claim 12, wherein the chitosan is of a viscosity grade of about 630 cp and the gelatin has a bloom number of about 80 to about 350.

* * * * *